United States Patent [19]

Miller

[11] Patent Number: 4,944,397
[45] Date of Patent: Jul. 31, 1990

[54] DISPOSABLE COVERED NEEDLE FOR SYRINGE

[75] Inventor: Ernest C. Miller, Jacksonville, Fla.

[73] Assignee: University Medical Center, Inc., Jacksonville, Fla.

[21] Appl. No.: 414,283

[22] Filed: Sep. 29, 1989

Related U.S. Application Data

[63] Continuation-in-part of Ser. No. 197,143, May 23, 1988, Pat. No. 4,886,503.

[51] Int. Cl.⁵ .............................................. B65D 85/24
[52] U.S. Cl. .................................. 206/365; 206/633; 604/198; 604/263
[58] Field of Search ................ 206/365, 633; 604/192, 604/198, 263

[56] References Cited

U.S. PATENT DOCUMENTS

| | | | |
|---|---|---|---|
| 3,989,045 | 11/1976 | Van Eck | 604/192 |
| 4,627,843 | 12/1986 | Raines | 604/263 |
| 4,643,722 | 2/1987 | Smith, Jr. | 206/365 |
| 4,664,259 | 5/1987 | Landis | 206/365 |
| 4,747,836 | 5/1988 | Luther | 604/263 |
| 4,838,871 | 6/1989 | Luther | 604/192 |

FOREIGN PATENT DOCUMENTS

| | | | |
|---|---|---|---|
| 3713754 | 11/1988 | Fed. Rep. of Germany | 604/198 |
| 8800477 | 1/1988 | PCT Int'l Appl. | 604/192 |
| 1125568 | 8/1968 | United Kingdom | 206/365 |

*Primary Examiner*—Jimmy G. Foster
*Attorney, Agent, or Firm*—Arthur G. Yeager

[57] ABSTRACT

A covered needle assembly having a needle member and a cover member pivotably connected to each other, the cover member having a long narrow opening for the needle to pass through when the cover member is pivoted away from the needle when ready for use, the opening being covered by a manually strippable tape which is removed prior to use of the needle; one embodiment providing a means to render the needle inserviceable after use.

16 Claims, 3 Drawing Sheets

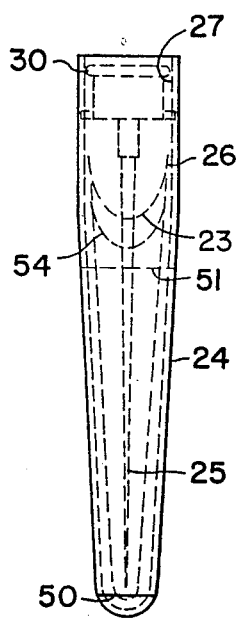
FIG 1
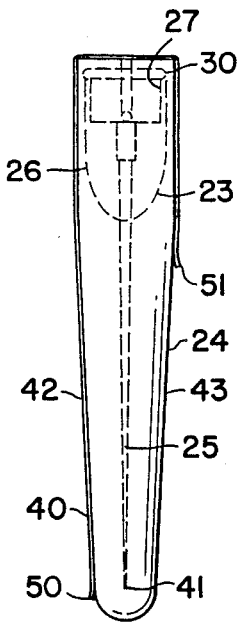
FIG 2
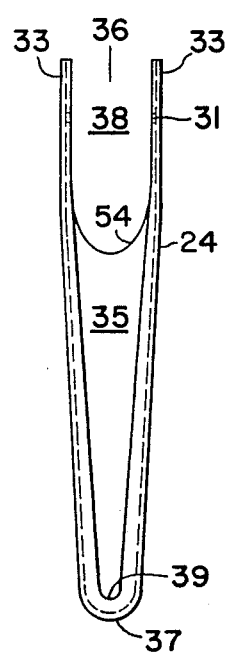
FIG 3
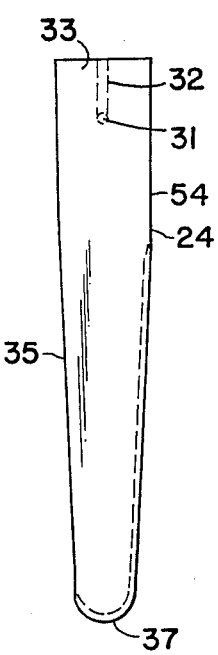
FIG 4
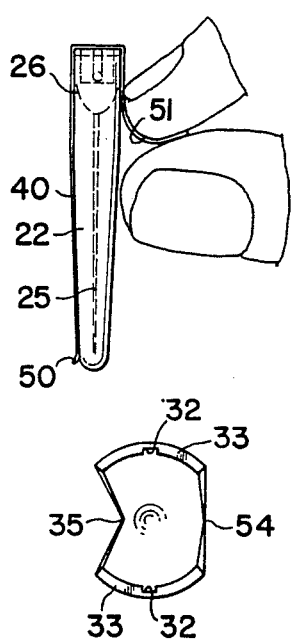
FIG 11
FIG 5
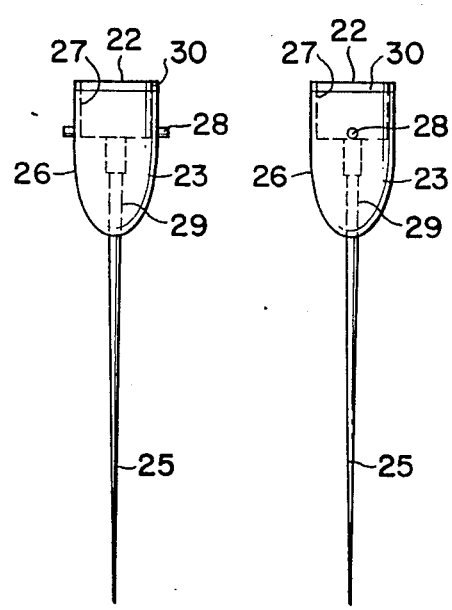
FIG 6    FIG 7
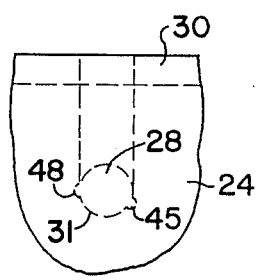
FIG 8

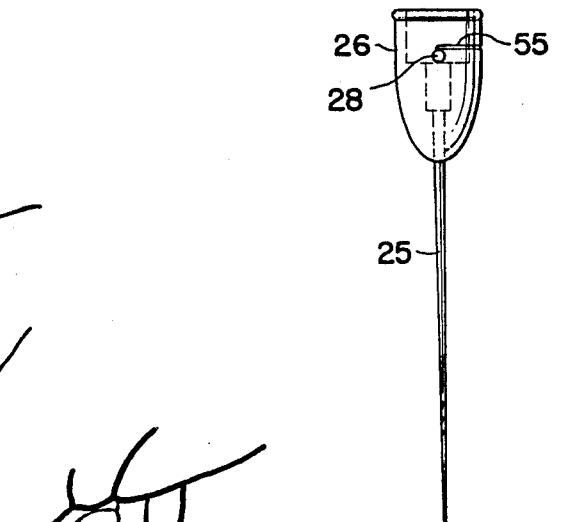
FIG 16
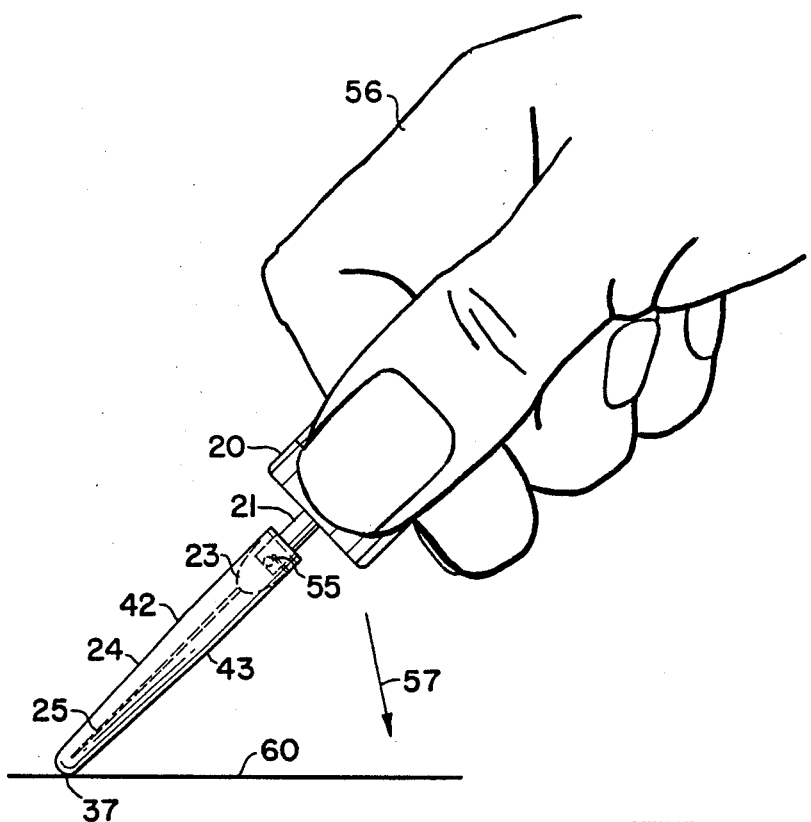
FIG 17
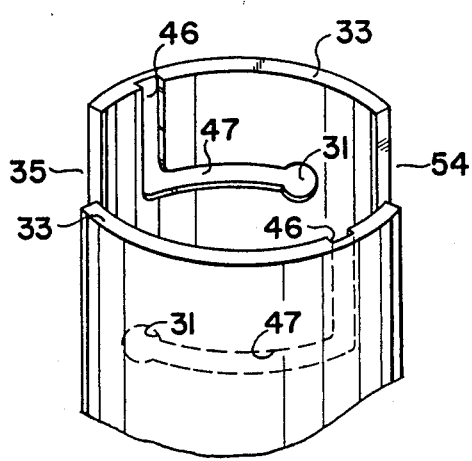
FIG 9
FIG 10
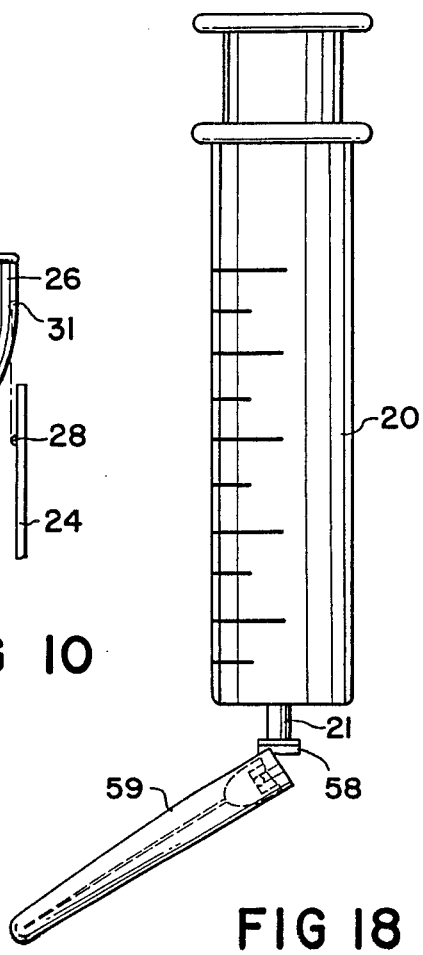
FIG 18

DISPOSABLE COVERED NEEDLE FOR SYRINGE

This is a continuation-in-part of patent application Ser. No. 07/197,143 filed May 23, 1988 by Ernest C. Miller now U.S. Pat. No. 4,886,503.

BACKGROUND OF THE INVENTION

A perennial problem with the use of hypodermic syringes in the past was the necessity to sterilize many syringes and needles while keeping the needle sharp. When the of disposable needles came into existence, the problems of sterilization were greatly reduced, and when disposable syringes were suggested most of the problems of sterilization and dull needles disappeared. Nevertheless, one problem remained and that involved the medical person using the syringe, who, the carelessness, frequently was stabbed by a used needle. Although this was serious when dealing with patients having certain infectious diseases the problem was greatly magnified when AIDS was recognized as a prevalent disease transmitted by intimate mixing of blood or other body fluids of an infected person with that of an uninfected person. The lack of a sure cure for AIDS has led to many safeguard procedures to protect medical personnel from inadvertent infection. Among the procedures the are those relating to safe use of a syringe and needle for injections and/or the taking of blood samples.

Among the prior art devices for prevention of needle punctures are several types. U.S. Pat. No. 3,306,290 to Weltman discloses a spring biased needle which retracts completely inside the syringe body when not in use. The most simple device is that typified by U.S. Pat. No. 4,654,034 to Masters et al., which is merely a funnel entrance cover for a needle which is removed for use of the needle and replaced after use of the needle. Devices such as those of U.S. Pat. Nos. 4,610,667 and 4,623,336 to Pedicano et al. where the funnel-top cover has a hinged cap which is closed with the used needle inside so as to prevent inadvertent punctures by those handling the trash containing disposable needles. Disclosed in U.S. Pat. No. 4,659,330 to Nelson et al., is a needle guard attachable to a syringe to cover the needle, and to permit the cover to pivot away from the needle when being used, and to be returned to cover the needle after use. My pending application Ser. No. 07/197,143 filed May 23, 1988 discloses and claims a covered needle in which the cover is pivotable to cause plastic film over a slit in the cover to be ruptured and thereby expose the needle for medical use. All of these devices have certain virtues, but only the needle of my pending patent application provides adequate safety from self-puncture. That needle does not have the best design for sterilization and handling, which the present invention provides.

It is an object of this invention to provide an improved disposable covered needle for a syringe. It is another object of this invention to provide an improved pivotable cover that virtually eliminates possibilities for inadvertent punctures by contaminated needles, while providing a unitized structure that is easily sterilized and convenient to use, and has the capability of being made unuseable. Still other objects will become apparent from the more detailed description which follows.

SUMMARY OF THE INVENTION

This invention relates to a disposable covered needle for releasable attachment to a syringe having a short tubular inlet/exi-t pipe; said covered needle including a needle member having a hollow needle with a free end and an encased end, said encased end being embedded in a socket having a top opening recess to engage said inlet/exit pipe and a passageway to connect said recess to the hollow of said needle; a cover member that is an elongated sheath enclosing said needle and pivotably attached to said socket and having an elongated lengthwise narrow opening structured and adapted to permit said needle to pass therethrough when said cover member is pivoted away from enclosing said needle; and a manually strippable tape which has been bonded to or adhesively attached to the outside of said cover member and to said socket so as to cover said narrow opening in said cover member and said top opening of said recess in said socket.

In preferred embodiments of this invention the pivot means between the needle member and the cover member includes pins projecting outwardly from one of the members to engage holes or recesses in the other of the members. In another preferred embodiment the cover member includes two longitudinal generally parallel, planar sides, one of which includes the elongated narrow opening through which the needle is exposed when the cover member is pivoted away from the needle; and the other of which includes a short narrow opening to provide room for the cover member to be pivoted through a large obtuse angle when the needle is exposed. The strippable tape covers both openings and extends across the top opening of the socket head, to make an enclosed cover member with the needle member inside. In another embodiment, the syringe after use, may be pressed at an angle so as to break the socket head of the needle member and render it useless for further applications.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is a front elevational view of the covered needle assembly of this invention;

FIG. 2 is a side elevational view of the covered needle assembly of this invention;

FIG. 3 is a front elevational view of the cover member;

FIG. 4 is a side elevational view of the cover member;

FIG. 5 is an enlarged top plan view of the cover member of FIG. 4;

FIG. 6 is a front elevational view of the needle member;

FIG. 7 is a side elevational view of the needle member;

FIG. 8 is a side elevational view of a first alternative embodiment of the cover member having a rotational lock arrangement;

FIG. 9 is an enlarged perspective view of a second alternative embodiment of the pivot eye of the cover member;

FIG. 10 is a front elevational view of the cover member and the needle member showing an alternative arrangement of the pivot means;

FIG. 11 is a side elevational view of the covered needle assembly showing the step of partial removal of the enclosing cover tape;

FIG. 16 is a side elevational view of the needle member having a breakable socket head;

FIG. 17 is a schematic view of a syringe having the breakable socket head of FIG. 16, and how it is easily broken; and FIG. 18 is a side elevational view of the syringe and socket head of FIG. 17 after it is broken.

DETAILED DESCRIPTION OF THE INVENTION

Figure 15:
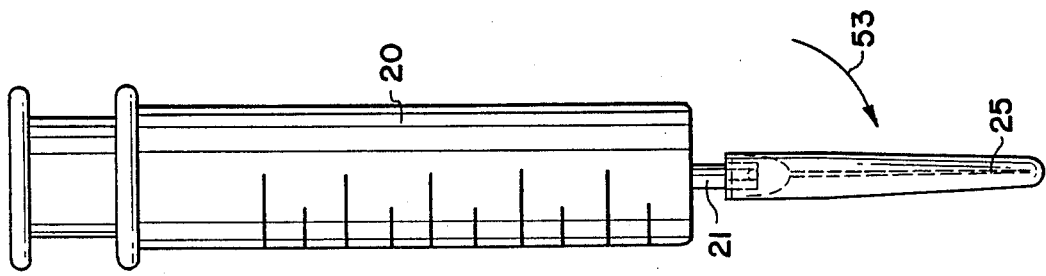
FIG. 15 is a front elevational view of the syringe and needle assembly of FIG. 13 after use and after returning the cover to its position of covering the needle.

The needle cover of this invention can best be understood by reference to FIGS. 1–9 of the attached drawings for the structural features and by reference to FIGS. 10–14 for the manner in which the covered needle is used.

In FIGS. 1–6 there are illustrated various views of the parts of the disposable covered needle of this invention. The entire assembly consists of two cooperating parts: needle member 23 and cover member 24. These two parts are joined together by pivot means, illustrated by pivot pins 28 and pivot recesses or eyes 31, providing the opportunity for cover member 24 to pivot away from needle member 23 as may be seen in FIG. 13 which will be described below.

Needle member 23 includes a cup-shaped socket head 26 having an internal recess 27 and an open top 22 to receive the spout 21 of a medical syringe 20. This normally is a friction connection, but may include a short screw thread or other positive joining means. Hollow needle 25 has one end 29 embedded in head 26 with the other end 41 being free and available for insertion into the body of a patient to perform an intravenous injection or to draw a sample of blood or other body fluid. Recess 27 communicates with the hollow of needle 25. The upper portion of head 26 preferably includes a small flange 30 serving as a finger grip for pushing the covered needle assembly onto spout 21 of syringe 20. Flange 30 may be omitted entirely, but if used it is only slightly larger in diameter than that of head 26 so as not to obstruct the pivoting of cover 24 about needle member 23. In the embodiment of FIGS. 1–7 head 26 also contains two pivot pins 28 extending out opposite sides thereof and adapted to suspend cover member 24 therefrom by way of recesses or eyes 31.

Cover member 24 is an elongated tubular structure having an upper open end 36 and a lower closed end 37. On opposite sides of open end 36 are arms 33, each containing a pivot recess 31 for attachment to a pivot pin 28 on needle member 23. Eye 31 is adjacent the top edge of arm 33 and is joined thereto by a narrow groove 32 through which pivot pin 28 may slide. Groove 32 serves the purpose of providing a way to assemble cover member 24 to needle member 23. It is preferred that recess 31 and groove 32 not extend through the walls of arms 33 to help the entire assembly to be closed and remain sterilized when attaching the assembly to a syringe. Arms 33 will spring apart under a little pressure to allow pivot pin 28 to pass through to reach its proper position in eye 31, Whereupon arms 33 will spring back to their normal position which will hold cover member 24 in place unless there is deliberate attempt to separate cover member 24 from needle member 23. If cover member 24 is made of a sufficiently flexible plastic, it may not be necessary to include grooves 32. Assembly could then proceed by merely spreading arms 33 apart sufficiently to snap over pivot pins 28. Arms 33 are curved as seen in FIG. 5 to fit snugly around socket head 23 and must flex away from socket head 23 when cover member 24 is pivoted away from needle member 23. This provides a type of "snapfit" causing needle member 23 and cover member 24 to remain in the closed position until forced to open by the pivoting of cover member 24. It is to be understood that eye 31 may in some embodiments be an opening through the wall of arm 33 but it should be recognized that such an opening provide an avenue for contaminating germs and therefore is not preferred.

Figure 14:
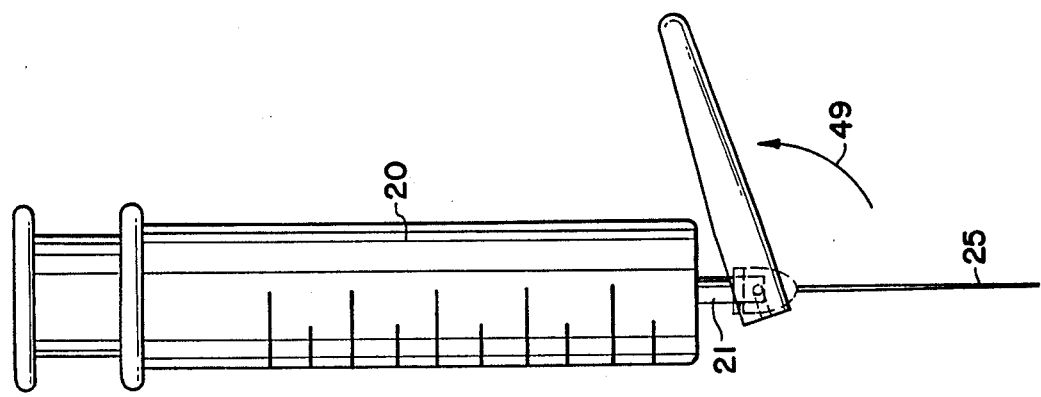
FIG. 14 is a front elevational view of the syringe and needle assembly of FIG. 12 illustrating the fully pivoted position of the cover member ready for medical use.

An elongated narrow opening 35 extends from the open top 36 to adjacent closed end 37 along one side 42 of cover member 24. The upper end 38 of opening 35 is open and the lower end 39 of opening 35 is closed. Opening 35 is sufficiently long to allow needle 25 to be exposed when cover member 24 is pivoted away as in FIG. 13. The width of opening 35 need only be enough to allow needle 25 to swing through without touching cover member 24. On the opposite side 43 of cover member 24 is a short opening 54 which is long enough merely to clear the lower end of head 26 where needle 25 is embedded therein 29. This opening is important only in permitting a fully pivoted position of cover member 24 as seen in FIG. 14. Without opening 54 the pivoting would be restricted. Over the outside of openings 35 and 54 there is attached an elongated cover tape 40 which is manually strippable from cover member 24. The position of tape 40 is shown in FIGS. 1 and 2 in solid lines extending as one continuous strip from 50 to 51. Tape 40 may be attached by pressure-sensitive adhesive or it may be heat bonded to cover member 24 and would be attached normally as a final step after joining cover member 24 to needle member 23. It is only important that tape 40 be impervious to air and moisture so as to maintain the sterility of the needle 25, and be manually strippable when ready for use. Preferably, tape 40 would extend from 50 over the open top 22 of head 26 and down the opposite side of cover member 24 to 51. Tape 40 covers all openings in cover member 24 and needle member 24 to provide protection against contamination when the covered needle assembly is attached to syringe 20. To assist in a secure covering by tape 40 it is preferable if two opposite sides 42 and 43 of cover member 24 are substantially planar and parallel to each other at least through the portions necessary to cover an opening or to provide a solid anchor. Side 41 preferably is planar to the lower end 39 of opening 35. Tape 40 must, of course, be wide enough to cover opening 35 and top opening 22. Flat sides 42 and 43 may be molded to be flat or cover member 24 may be ground to provide flat sides 42 and 43. Flange 30 of needle member 23 may also be molded or ground to provide flat surfaces adjoining flat sides 42 and 43 so as to have better base for sealing tape 40.

In FIGS. 8–10 there are shown alternative embodiments for the needle assembly of this invention. In FIG. 9 entrance groove 32, through which pivot pin 28 travels to reach hole 31 when assembling cover member 24 to needle member 23, is modified to an L-shaped groove 44 having a vertical leg 46 and a horizontal leg 47. The purpose of this arrangement is to provide additional safety against the possibility of needle member 23 inadvertently pivoting while the entire assembly 22 is being attached to syringe 20. The length of horizontal leg 47 is coordinated with the width of opening 35 so that if an inadvertent pivoting should occur while pushing pivot pin through vertical leg 46, needle 25 will not be aligned with opening 35 and will be prevented from pivoting outwardly. By twisting cover member 24 to move pivot pin 28 through horizontal leg 47 to hole 31, pivot pins 28 become properly aligned to allow needle 25 to pivot outwardly through opening 35. Other types of structures can be used to provide such a safeguard.

Figure 13:
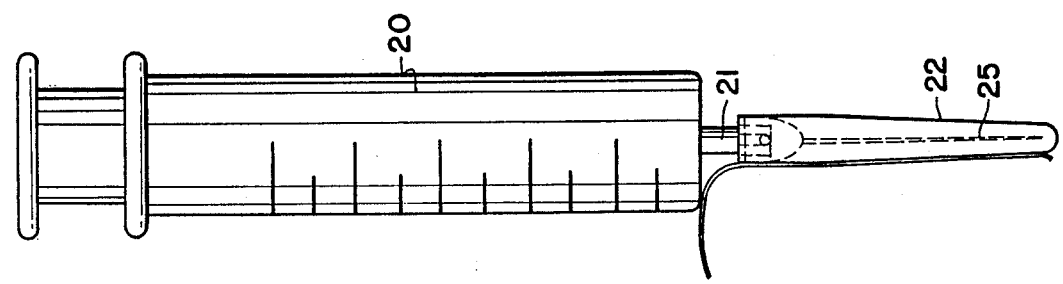
FIG. 13 is a front elevational view of the syringe with the partially uncovered needle assembly of FIG. 12 attached thereto.
Figure 12:
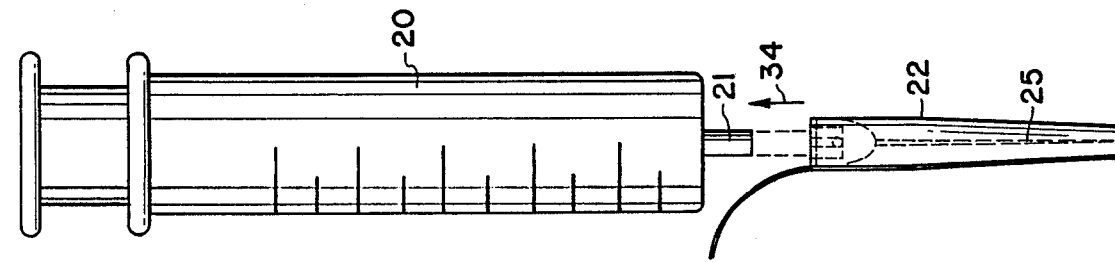
FIG. 12 is a front elevational view of a syringe with the partially uncovered needle assembly of FIG. 11 ready for attachment thereto.

Pivot pin 28 and recess 31 may be fashioned so as to provide a bias toward maintaining cover member 24 either in the fully open position of FIG. 13 or the fully closed position of FIGS. 12 and 14, to prevent cover member 24 from swinging indiscriminately. A typical procedure is that shown in FIG. 8 where pivot pin 28 and recess 31 are fashioned with corresponding protuberances on pin 28 and recesses on hole 31. The combination located at 45 may, for example, maintain a bias toward keeping cover member 24 in a closed position, while the combination at 48 will bias cover 24 to remain in an open position. Such a combination of a small protuberance on pin 28 and a small recess in the perimeter of recess 31 results in an operational advantage whereby the operator of the syringe can feel the cover member 24 snap into place. It has been described above that a similar bias toward cover member 24 being closed over needle member 23 exists by reason of the concavity of the upper end 36 of cover member 24 fitting snugly over the convex outer surface of head 26. Other temporary bias procedures can be employed.

In FIG. 10 there is shown the manner in which pivot pins 28 and pivot recesses 31 may be reversed from those of FIGS. 1–7. Here pins 28 project toward each other from the inside surfaces of arms 33. Correspondingly, recesses 31 are positioned on opposite sides of the outside surface of cup-shaped head 26 to receive pins 28 therein. If arms 33 are not sufficiently springy to flex outwardly to allow pins 28 to pass over the surface of head 26, it may be feasible to provide grooves 52 in head 26 to facilitate locating and engaging pins 28 into recesses 31.

In FIGS. 11–15 there are shown the steps involved in using the device of this invention. In FIG. 11 tape 40 is removed from a portion of needle assembly 22. In FIG. 12 partially opened needle assembly 22 is positioned ready to be assembled onto syringe spout 21 by moving upward in the direction of arrow 34. In FIG. 13 needle assembly 22 has been pushed onto spout 21 to a tight frictional fit. In FIG. 14 tape 40 has been stripped away from cover member 24 and cover member 24 has been pivoted in the direction of arrow 49 enough for needle 25 to be uncovered for medical use. It may be preferable not to strip tape 40 completely away from cover member 24 so as to keep it available for covering opening 35 after the needle 25 has been used and returned to a safe position as in FIG. 15 for disposal. In FIG. 15 cover member 24 has been pivoted in the direction of arrow 53 to its original position for it to be removed safely from syringe 20 and thrown away. As mentioned above it may be found preferable to press tape 40 into place after recovering needle 25 as in FIG. 15 before disposing of the used needle.

The advantages of including tape 40 are that (1) it provides a positive safeguard against inadvertently pivoting cover member 24 away from needle member 23 exposing needle 25 when not desired, (2) it provides a means to sterilize the covered needle assembly at the manufacturing site and to cover the sterilized assembly so that handling of the assembly does not contaminate the needle, (3) it provides a safe means to handle the assembly in attaching it to the syringe before use, and it is a safeguard against exposing the needle too soon by stripping away only the short portion of the tape as shown in FIG. 10 because the cover cannot be pivoted until the tape is stripped from the opposite side where narrow opening 35 is located.

In FIGS. 16–18 there is shown an embodiment that will provide even further safety from contamination by a used needle. In this embodiment needle member 23 is shown as in FIG. 6, except that it is modified by a weakening groove or score line 55 about half way around the circumference of socket head 26 at about the level of pivot pins 28. The line 55 generally will lie in a plane perpendicular to the longitudinal axis of the needle and the syringe. When the syringe and needle have been used and the cover member pivoted back to cover needle 25 (e.g., as in FIG. 15) the medical person using the syringe may position the syringe in his or her hand with closed end 37 against a table top 60 or other solid surface and push downwardly in the direction of arrow 57 to break the socket head 26 along weakened line 55 to the broken equipment of FIG. 18. Depending on the position of weakening line 55 spout 21 may or may not be easily removed from the broken portion 58 of socket head 26. If it is easily removed, syringe 20 may be separated from the broken needle assembly and resterilized. It is more likely that the syringe and needle member after being broken will both be considered expendible and thrown away. After using the needle the cover number 24 may be closed over the exposed needle 25 and broken all in one motion as shown in FIG. 17.

Preferably, weakening line 55 is on the same side as side 43 of cover member 24 so that when the breaking force is applied as in FIG. 17, needle 25 will be pressed against a solid wall of cover member 24 and not against the long opening 35.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

I claim:

1. A throw-away covered needle for releasable attachment to a syringe having a short tubular inlet/exit pipe, said covered needle including a needle member having a hollow needle with a free end and an encased end, said encased end being embedded in a socket having a top opening recess to engage said inlet/exit pipe and a passageway to connect said recess to the hollow of said needle; a cover member that is an elongated sheath enclosing said needle and pivotably attached to said socket and having an elongated lengthwise narrow opening structured and adapted to permit said needle to pass therethrough when said cover member is pivoted away from enclosing said needle; and a manually strippable adhesive tape attached to the outside of said cover member and to said socket so as to cover said narrow opening in said cover member and said top opening of said recess in said socket.

2. The covered needle of claim 1 wherein said cover member is pivotably attached to said pivot pins by a pivot recess for each said pin in said sheath pivotably fitting around pivot pins projecting outwardly from said socket.

3. The covered needle of claim 2 wherein said sheath includes a groove from said pivot recess to the nearest edge of said sheath and adapted to guide said pivot pins to pass therethrough to said pivot recess.

4. The covered needle of claim 3 wherein said groove includes a vertical portion parallel to said needle joined to a horizontal portion perpendicular to said needle which terminates in said pivot recess.

5. The covered needle of claim 1 wherein said pivot pins and the cooperating portions of said cover member include a small protuberance on said pin to cooperate with a small recess on said cover member positioned to bias said needle to lie along the lengthwise axis of said sheath.

6. The covered needle of claim 1 wherein said pivot pins are permanently attached to said cover member and said socket is structured with two recesses adapted to operatively engage said pins.

7. The covered needle of claim 1 wherein said cover member has two lengthwise generally parallel planar sides, one of which includes said lengthwise narrow opening.

8. The covered needle of claim 7 wherein said tape extends along said two generally parallel sides from the terminus of said narrow opening on one of said sides adjacent the tip of said needle upwards and over said top opening recess, and down a substantial portion of the other of said sides.

9. The covered needle of claim 1 wherein said socket includes a semicircumferential weakening groove around said socket generally in a plane perpendicular to said needle.

10. A safety covered needle for use on a medical syringe having a short tubular spout; said covered needle comprising a needle member and a cover member pivotally connected to said needle member; said needle member including cup-shaped head with an interior recess with an upwardly facing opening adapted to frictionally engage said spout, a hollow needle having a free end and having the other end embedded in said head, a passageway in said head joining said recess and said other end of said needle; said cover member being an elongated sheath having an upper open end and a lower closed end and a longitudinal axis corresponding to the hollow of said needle, an elongated narrow opening extending from said open end to a closed end adjacent said lower end of said sheath; pivot means located adjacent said head and said open end of said sheath structured and adapted to permit said sheath to pivot away from said needle to expose said needle; and a manually strippable tape adhesively attached to said sheath and said head to cover said elongated narrow opening and the opening of said interior recess in said head.

11. The covered needle of claim 10 wherein said sheath is a thin walled tubular plastic article with a narrow slotted opening through said wall extending from said upper open end to adjacent said lower end of said sheath.

12. The covered needle of claim 10 wherein said pivot means includes recesses adjacent said upper open end of said sheath operatively engageable with pins projecting outwardly from opposite sides of said head.

13. The covered wall of claim 12 which additionally comprises a narrow groove from each said recess to a nearby edge of said sheath along an L-shaped path, one leg of said L being substantially parallel with said axis and the other leg being substantially perpendicular to said axis.

14. The covered needle of claim 10 wherein said pivot means includes a pair of inwardly projecting pins attached to opposite sides of said sheath adjacent said upper open end operatively engageable with corresponding recesses in the outside of said cup-shaped head.

15. The covered needle of claim 10 wherein the outside of said cover member is fashioned with two opposite planar substantially parallel walls extending at least a portion of the total length of said cover member, one of said walls having said elongated narrow opening therethrough; and wherein said tape is adhesively attached in a single continuous strip from the end of said narrow opening up to said head, across said opening of said interior recess, and down a substantial portion of said side opposite to the side containing said narrow opening.

16. The covered needle of claim 10 wherein said cup-shaped head includes a semicircumferential weakening line around the outside of said head adjacent said pivot means, generally in a plane perpendicular to said longitudinal axis.

* * * * *